(12) United States Patent
Serhan

(10) Patent No.: US 7,132,451 B2
(45) Date of Patent: *Nov. 7, 2006

(54) INHIBITION OF TNF-α-INITIATED NEUTROPHIL RESPONSE

(76) Inventor: Charles N. Serhan, 23 Smith St., Needham, MA (US) 02492

( * ) Notice: Subject to any disclaimer, the term of this patent is extended or adjusted under 35 U.S.C. 154(b) by 0 days.

This patent is subject to a terminal disclaimer.

(21) Appl. No.: 10/794,153

(22) Filed: Mar. 5, 2004

(65) Prior Publication Data

US 2004/0192785 A1 Sep. 30, 2004

Related U.S. Application Data

(63) Continuation of application No. 10/044,740, filed on Jan. 11, 2002, now Pat. No. 6,710,084, which is a continuation of application No. 09/525,291, filed on Mar. 14, 2000, now Pat. No. 6,387,953.

(60) Provisional application No. 60/125,205, filed on Mar. 18, 1999.

(51) Int. Cl.
*A61K 31/20* (2006.01)
(52) U.S. Cl. ............... 514/560; 514/213; 514/224; 514/219; 514/552; 514/558
(58) Field of Classification Search ............. 514/558, 514/560, 213, 552, 224, 219
See application file for complete search history.

(56) References Cited

U.S. PATENT DOCUMENTS

| 5,441,951 | A | 8/1995 | Serhan | |
|---|---|---|---|---|
| 6,387,953 | B1 | 5/2002 | Serhan | |
| 6,703,423 | B1 * | 3/2004 | Serhan | 514/560 |
| 6,710,084 | B1 | 3/2004 | Serhan | |
| 6,720,354 | B1 * | 4/2004 | Serhan | 514/552 |
| 6,864,288 | B1 * | 3/2005 | Serhan | 514/552 |
| 6,927,238 | B1 * | 8/2005 | Serhan | 514/560 |

FOREIGN PATENT DOCUMENTS

| WO | WO 94/29262 | 12/1994 |
|---|---|---|
| WO | WO 95/01179 | 1/1995 |
| WO | WO 98/11049 | 3/1998 |

OTHER PUBLICATIONS

Serhan, C.N., J.Z. Haeggström, and C.C. Leslie. 1996. Lipid mediator networks in cell signaling: update and impact of cytokines. *FASEB J.* 10:1147-1158.
Weiss, S.J. 1989. Tissue destruction by neutrophils. *N. Engl. J. Med.* 320:365-376.
Marucha, P.T., R.A. Zeff, and D.L. Kreutzer. 1991. Cytokine-induced IL-1β gene expression in the human polymorphonuclear leukocyte: transcriptional and post-transcriptional regulation by tumor necrosis factor and IL-1. *J. Immunol.* 147:2603-2608.
Lloyd, A.R., and J.J. Oppenheim. 1992. Poly's lament: the neglected role of the polymorphonuclear neutrophil in the afferent limb of the immune response. *Immunology Today* 13:169-172.
Hachicha, M., P.H. Naccache, and S.R. McColl. 1995. Inflammatory microcrystals differentially regulate the secretion of macrophage inflammatory protein 1 and interleukin-8 by human neutrophils: A possible mechanism of neutrophil recruitment to sites of inflammation in synovitis. *J. Exp. Med.* 182:2019-2025.
Hansen, P.R. 1995. Role of neutrophils in myocardial ischemia and reperfusion. *Circulation* 91:1872-1885.
Takano, T., S. Fiore, J.F. Maddox, H.H. Brady, N.A. Petasis, and C.N. Serhan. 1997. Aspirin-triggered 15-epi-lipoxin $A_4$ and $LXA_4$ stable analogs are potent inhibitors of acute inflammation: Evidence for anti-inflammatory receptors. *J. Exp. Med.* 185:1693-1704.
Clària, J., and C.N. Serhan. 1995. Aspirin triggers previously undescribed bioactive eicosanoids by human endothelial cell-leukocyte interactions. *Proc. Natl. Acad. Sci. USA* 92:9475-9479.
Lee, T.H., C.E. Horton, U. Kyan-Aung, D. Haskard, A.E. Crea, and B.W. Spur. 1989. Lipoxin $A_4$ and lipoxin $B_4$ inhibit chemotactic responses of human neutrophils stimulated by leukotriene $B_4$ and N-formyl-L-methionyl-L-leucyl-L-phenylalanine. *Clin. Sci.* 77:195-203.
Serhan, C.N. 1994. Lipoxin biosynthesis and its impact in inflammatory and vascular events. *Biochim. Biophys. Acta* 1212:1-25.
Papayianni, A., C.N. Serhan, M.L. Phillips, H.G. Rennke, and H.R. Brady. 1995. Transcellular biosynthesis of lipoxin $A_4$ during adhesion of platelets and neutrophils in experimental immune complex glomerulonephritis. *Kidney Int.* 47:1295-1302.
Chavis, C., I. Vachier, P. Chanez, J. Bousquet, and P. Godard. 1996. 5(S),15(S)-Dihydroxyeicosatetraenoic acid and lipoxin generation in human polymorphonuclear cells: dual specificity of 5-lipoxygenase towards endogenous and exogenous precursors. *J. Exp. Med.* 183:1633-1643.
Thomas, E., J.L. Leroux, F. Blotman, and C. Chavis. 1995. Conversion of endogenous arachidonic acid to 5,15-diHETE and lipoxins by polymorphonuclear cells from patients with rheumatoid arthritis. *Inflamm. Res.* 44:121-124.
Serhan, C.N., J.F. Maddox, N.A. Petasis, I. Akritopoulou-Zanze, A. Papayianni, H.R. Brady, S.P. Colgan, and J.L. Madara. 1995. Design of lipoxin $A_4$ stable analogs that block transmigration and adhesion of human neutrophils. *Biochemistry* 34:14609-14615.
Gronert, K., S.P. Colgan, and C.N. Serhan. 1998. Characterization of human neutrophil and endothelial cell ligand-operated extracellular acidification rate by microphysiometry: impact of reoxygenation. *J. Pharmacol. Exp. Ther.* 285:252-261.
Tessier, P.A., P.H. Naccache, I. Clark-Lewis, R.P. Gladue, K.S. Neote, and S.R. McColl. 1997. Chemokine networks in vivo: involvement of C-X-C and C-C chemokines in neutrophil extravasation in vivo in response to TNF-α. *J. Immunol.* 159:3595-3602.
Tsujii, M., S. Kawano, S. Tsuji, H. Sawaoka, M. Hori, and R.N. DuBois. 1998. Cyclooxygenase regulates angiogenesis induced by colon cancer cells. *Cell* 93:705-716.

(Continued)

*Primary Examiner*—Dwayne Jones
(74) *Attorney, Agent, or Firm*—Scott D. Rothenberger; Dorsey & Whitney LLP

(57) ABSTRACT

The impact of lipoxin $A_4$ ($LXA_4$) and aspirin-triggered-lipoxins (ATL) was investigated in tumor necrosis factor (TNFα)-initiated neutrophil (PMN) responses in vitro and in vivo using metabolically stable LX analogs. At concentrations as low as 1–10 nM, the $LXA_4$ and ATL analogs each inhibited TNFα-stimulated superoxide anion generation and IL-1β release by human PMN.

9 Claims, 7 Drawing Sheets

OTHER PUBLICATIONS

Shibuya, H., N. Ohkohchi, S. Tsukamoto, and S. Satomi. 1997. Tumor necrosis factor-induced, superoxide-mediated neutrophil accumulation in cold ischemic/reperfused rat liver. *Hepatology* 26:113-120.

Jaeschke, H., A. Farhood, and C.W. Smith. 1990. Neutrophils contribute to ischemia/reperfusion injury in rat liver *in vivo*. *FASEB J*. 4:3355-3359.

Dinarello, C.A. 1996. Biologic basis for interleukin-1 in disease. *Blood* 87:2095-2147.

Fiore, S., and C.N. Serhan. 1995. Lipoxin $A_4$ receptor activation is distinct from that of the formyl peptide receptor in myeloid cells: inhibition of CD11/18 expression by lipoxin $A_4$ lipoxin $A_4$ receptor interaction. *Biochemistry* 34:16678-16686.

Sin, Y.M., A.D. Sedgwick, E.P. Chea, and D.A. Willoughby. 1986. Mast cells in newly formed lining tissue during acute inflammation: a six day air pouch model in the mouse. *Ann. Rheum. Dis*. 45:873-877.

Maddox, J.F., M. Hachicha, T. Takano, N.A. Petasis, V.V. Fokin, and C.N. Serhan. 1997. Lipoxin $A_4$ stable analogs are potent mimetics that stimulate human monocytes and THP-1 cells via a G-protein linked lipoxin $A_4$ receptor. *J. Biol. Chem*. 272:6972-6978.

Isomaki, P., and J. Punnonen. 1997. Pro- and anti-inflammatory cytokines in rheumatoid arthritis. *Ann. Med*. 29:499-507.

Volpert, O.V., T. Fong, A.E. Koch, J.D. Peterson, C. Waltenbaugh, R.I. Tepper, and N.P. Bouck. 1998. Inhibition of angiogenesis by interleukin 4. *J. Exp. Med*. 188:1039-1046.

Moreland, L.W., S.W. Baumgartner, M.H. Schiff, E.A. Tindall, R.M. Fleischmann, A.L. Weaver, R.E. Ettlinger, S. Cohen, W.J. Koopman, K. Mohler, M.B. Widmer, and C.M. Blosch. 1997. Treatment of rehumatoid arthritis with a recombinant human tumor necrosis factor receptor (p75)-Fc fusion protein. *N. Engl. J. Med*. 337:141-147.

Marriott, J.B., M. Westby, and A.G. Dalgleish. 1997. Therapeutic potential of TNF-α inhibitors old and new. *DDT* 2:273-282.

Saleem, S., Z. Dai, S.N. Coelho, B.T. Konieczny, K.J.M. Assmann, F.K. Baddoura, and F.G. Lakkis. 1998. IL-4 is an endogenous inhibitor of neutrophil influx and subsequent pathology in acute antibody-mediated inflammation. *J. Immunol*. 160:979-984.

Lehn, M., W.Y. Weiser, S. Engelhorn, S. Gillis, and H.G. Remold. 1989. IL-4 inhibits $H_2O_2$ production and antileishmanial capacity of human cultured monocytes mediated by IFN-γ. *J. Immunol*. 143:3020-3024.

Takano, et al., Neutrophil-Mediated Changes in Permeability are Inhibited by Topical Application of Aspirin-Triggered 15-ept-Lipoxin A4 and Novel Lipoxin B4 Stable Analogs, *Journal of Clinical Investigations*, vol. 101, No. 4, pp. 819-826 (Feb. 1998).

Gewirzt, et al., Pathogen-Induced Chemokine Secretion from Model Intestinal Epithelium is Inhibited by Lipoxin A4 Analogs, *Journal of Clinical Investigations*, vol. 101, No. 9, pp. 1860-1869 (May 1998).

* cited by examiner

INHIBITION OF TNF-α-INITIATED NEUTROPHIL RESPONSE

CROSS-REFERENCE TO RELATED APPLICATIONS

This application claims priority to U.S. Ser. No. 10/044,740, filed Jan. 11, 2002 now U.S. Pat. No. 6,710,084, which is a continuation application of U.S. Ser. No. 09/525,291, filed Mar. 14, 2000 now U.S. Pat. No. 6,387,953 which claims priority to U.S. Provisional Patent Application No. 60/125,205 filed Mar. 18, 1999, the contents of which are incorporated herein by reference.

STATEMENT REGARDING FEDERALLY SPONSORED RESEARCH

The work leading to this invention was supported in part by grants GM-38765 and P01-DR50305 from the National Institutes of Health. The U.S. Government therefore may have certain rights in the invention.

BACKGROUND OF THE INVENTION

Lipid and protein mediators of inflammation such as cytokines and chemokines have a profound impact on the formation and actions of each other (Serhan, C. N., J. Z. Haeggström, and C. C. Leslie. 1996. Lipid mediator networks in cell signaling: update and impact of cytokines. *FASEB J.* 10:1147–1158). In particular, the cytokines TNFα and IL-1β play major roles in inflammation, septic shock and tissue injury. PMN perform a range of well-appreciated specialized functions, including chemotaxis, generation of reactive oxygen species and biosynthesis of potent lipid mediators (Weiss, S. J. 1989. Tissue destruction by neutrophils. *N. Engl. J. Med.* 320:365–376). In this regard, TNFα stimulates PMN to transcribe and release cytokines such as IL-1β, enhances leukotriene biosynthesis, and up-regulates adhesion molecules (Marucha, P. T., R. A. Zeff, and D. L. Kreutzer. 1991. Cytokine-induced IL-1β gene expression in the human polymorphonuclear leukocyte: transcriptional and post-transcriptional regulation by tumor necrosis factor and IL-1. *J. Immunol.* 147:2603–2608). Since PMN represent approximately 70% of the peripheral blood leukocytes and are in many instances the initial cell type recruited to interstitial sites, they are now considered a significant source of "proinflammatory" cytokines including TNFα and IL-1β. These as well as other PMN-derived cytokines and chemokines can, in turn, affect the course of inflammatory and immune responses (Lloyd, A. R., and J. J. Oppenheim. 1992. Poly's lament: the neglected role of the polymorphonuclear neutrophil in the afferent limb of the immune response. *Immunology Today* 13:169–172). In certain clinical settings, including respiratory distress syndrome, myocardial reperfusion injury, gout and rheumatoid arthritis, PMN contribute to ongoing damage of host tissues (Weiss, S. J. 1989. Tissue destruction by neutrophils. *N. Engl. J. Med.* 320:365–376; Hachicha, M., P. H. Naccache, and S. R. McColl. 1995. Inflammatory microcrystals differentially regulate the secretion of macrophage inflammatory protein-1 and interleukin-8 by human neutrophils: A possible mechanism of neutrophil recruitment to sites of inflammation in synovitis. *J. Exp. Med.* 182:2019–2025; Hansen, P. R. 1995. Role of neutrophils in myocardial ischemia and reperfusion. *Circulation* 91:1872–1885). Thus, it is of interest to understand the complex relationships between lipid mediators and TNFα-evoked PMN responses in order to gain insight for new approaches in controlling these events.

SUMMARY OF THE INVENTION

The present invention pertains to methods for modulating a disease or condition associated with TNFα initiated polymorphoneutrophil (PMN) inflammation. The methods include administration to a subject, an effective anti-inflammatory amount of a lipoxin analog having the formula described infra, such that the TNFα initated PMN inflammation is modulated.

The present invention also pertains to methods for treating TNFα initiated polymorphoneutrophil (PMN) inflammation in a subject. The methods include administration of an effective anti-inflammatory amount of a lipoxin analog described infra, such that TNFα initiated polymorphoneutrophil (PMN) inflammation is treated.

The present invention further pertains to methods for modulating a disease or condition associated with TNFα initiated cytokine activity in a subject. The methods include, administration of an effective anti-TNFα amount of a lipoxin analog described infra, such that a disease or condition associated with TNFα initiated cytokine activity, is modulated.

The present invention further relates to methods for treating TNFα initiated cytokine activity in a subject. The methods include administration of an effective anti-TNFα amount of a lipoxin analog described infra, such that TNFα initiated cytokine activity, e.g., inflammation, is treated.

The present invention also relates to methods for modulating a disease or condition associated with TNFα initiated IL-1β activity in a subject. The methods include administration of an effective anti-inflammatory amount of a lipoxin analog described infra, such that a disease or condition associated with TNFα initiated IL-1β, is modulated.

The present invention further pertains to methods for treating TNFα initiated IL-1β activity in a subject. The methods include administration of an effective anti-TNFα amount of a lipoxin analog described infra, such that TNFα initiated IL-1β activity, e.g., inflammation, is treated.

In preferred embodiments, the methods of the invention are performed in vitro or in vivo.

In another aspect, the present invention is directed to a packaged pharmaceutical composition for treating a the activity or conditions listed above in a subject. The packaged pharmaceutical composition includes a container holding a therapeutically effective amount of at least one lipoxin compound having one of the formulae described infra and instructions for using the lipoxin compound for treating the activity or condition in the subject.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
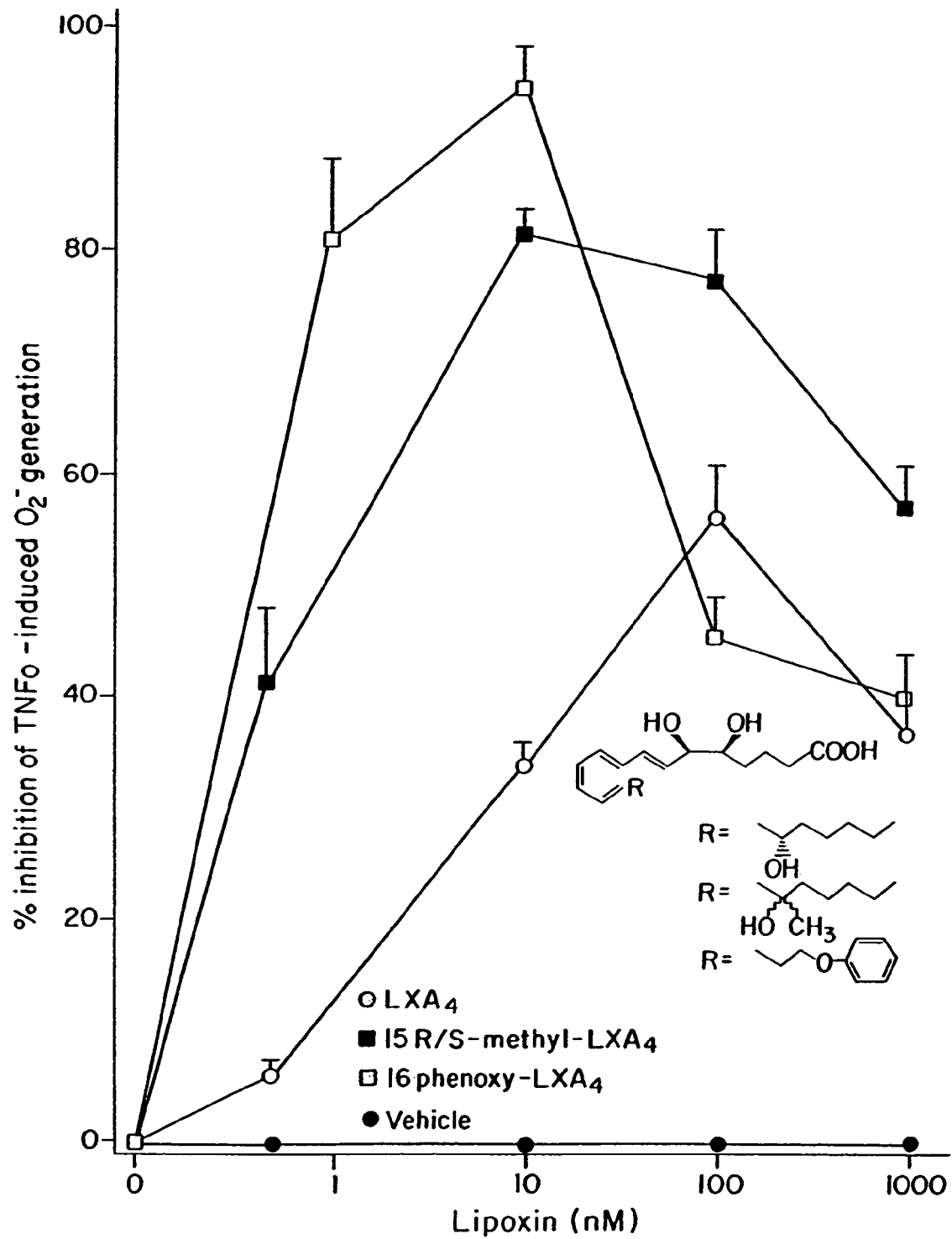
FIG. 1 shows that $LXA_4$ and ATL stable analogs inhibit TNFα-stimulated superoxide generation by human neutrophils. Human PMN were incubated with either vehicle alone or indicated concentrations of $LXA_4$, 15 R/S-methyl-$LXA_4$ or 16-phenoxy-$LXA_4$ for 5 min and then with TNFα (50 ng/ml) for an additional 10 min. Values are the mean±SEM for $LXA_4$ (n=3), 15 R/S-methyl-$LXA_4$ (n=4) or 16-phenoxy-$LXA_4$ (n=3). $LXA_4$ and analogs, at all concentrations tested, led to a statistically significant inhibition of TNFα-induced IL-1β appearance (p<0.01).

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The impact of lipoxin A$_4$ (LXA$_4$) and aspirin-triggered-lipoxins (ATL) was investigated in tumor necrosis factor (TNFα)-initiated neutrophil (PMN) responses in vitro and in vivo using metabolically stable LX analogs. At concentrations as low as 1–10 nM, the LXA$_4$ and ATL analogs each inhibited TNFα-stimulated superoxide anion generation and IL-1β release by human PMN. These LXA$_4$-ATL actions were time- and concentration-dependent and proved selective for TNFα, since these responses were not altered with either GM-CSF or zymosan-stimulated cells. TNFα-induced IL-1β gene expression was also regulated by both anti-LXA$_4$-receptor antibodies and LXA$_4$-ATL analogs. In murine air pouches, 15 R/S-methyl-LXA$_4$ dramatically inhibited TNFα-stimulated leukocyte trafficking, as well as the appearance of both macrophage inflammatory peptide-2 and IL-1β, while concomitantly stimulating IL-4 in pouch exudates. Together, these results indicate that both LXA$_4$ and ATL regulate TNFα directed neutrophil actions in vitro and in vivo and stimulate IL-4 in exudates, which plays a pivotal role in immune responses.

Abbreviations used in this application: ATL, aspirin-triggered-lipoxin; ATL analog, 15R/S-methyl-LXA$_4$-methyl ester; LX, lipoxin; LXA$_4$, 5S, 6R, 15S-trihydroxy-7,9,13-trans-11-cis-eicosatetraenoic acid; LXA$_4$ analog, 16 phenoxy-lipoxin A$_4$ methyl ester; 15-epi-LXA$_4$, 5S, 6R, 15R-trihydroxy-7,9,13-trans-11-cis-eicosatetraenoic acid; LT, leukotriene; MIP, macrophage inflammatory peptide; RA, rheumatoid arthritis. Suitable methods of preparation of lipoxin compounds can also be found, for example, in U.S. Pat. Nos. 5,411,951, 5,648,512, 5,650,435 and 5,750,354, incorporated herein by reference.

The contribution of leukotriene (LT[1])B$_4$ in inflammation is well established in view of its potent ability to attract PMN. Another series of bioactive lipid mediators termed lipoxins (LX) and aspirin-triggered lipoxins (ATL) each, within the nanomolar range, inhibits fMLP and LTB$_4$ stimulated PMN adhesion and transmigration and hence are proposed counter-regulatory signals operative in the resolution of inflammatory sites (Serhan, C. N., J. Z. Haeggström, and C. C. Leslie. 1996. Lipid mediator networks in cell signaling: update and impact of cytokines. *FASEB J.* 10:1147–1158; Takano, T., S. Fiore, J. F. Maddox, H. R. Brady, N. A. Petasis, and C. N. Serhan. 1997. Aspirin-triggered 15-epi-lipoxin A$_4$ and LXA$_4$ stable analogs are potent inhibitors of acute inflammation: Evidence for anti-inflammatory receptors. *J. Exp. Med.* 185:1693–1704; Clària, J., and C. N. Serhan. 1995. Aspirin triggers previously undescribed bioactive eicosanoids by human endothelial cell-leukocyte interactions. *Proc. Natl. Acad. Sci. USA* 92:9475–9479; Lee, T. H., C. E. Horton, U. Kyan-Aung, D. Haskard, A. E. Crea, and B. W. Spur. 1989. Lipoxin A$_4$ and lipoxin B$_4$ inhibit chemotactic responses of human neutrophils stimulated by leukotriene B$_4$ and N-formyl-L-methionyl-L-leucyl-L-phenylalanine. *Clin. Sci.* 77:195–203; Serhan, C. N. 1994. Lipoxin biosynthesis and its impact in inflammatory and vascular events. *Biochim. Biophys. Acta* 1212:1–25). In human tissues, three main pathways are known for LX generation. An intraluminal source of LX is exemplified by PMN-platelet interactions that utilize sequential transcellular biosynthetic routes with the PMN 5-lipoxygenase (LO) product LTA$_4$ and platelet 12-LO. The mucosal and/or interstitial source of these eicosanoids involves cell-cell interactions with leukocyte 5-LO and 15-LO present in, for example, eosinophils, gastrointestinal or tracheal epithelium that is controlled by IL-4 and IL-13 (reviewed in (Serhan, C. N., J. Z. Haeggström, and C. C. Leslie. 1996. Lipid mediator networks in cell signaling: update and impact of cytokines. *FASEB J.* 10:1147–1158)). The third and most recently elucidated also represents a novel mechanism of action for aspirin that triggers the endogenous biosynthesis of 15 R epimers of native LX, termed aspirin-triggered lipoxins (ATL), generated via transcellular biosynthesis (Clària, J., and C. N. Serhan. 1995. Aspirin triggers previously undescribed bioactive eicosanoids by human endothelial cell-leukocyte interactions. *Proc. Natl. Acad. Sci. USA* 92:9475–9479).

LX are generated during cell-cell interactions via transcellular biosynthesis, and are produced in vivo during angioplasty and in immune complex glomerulonephritis (Serhan, C. N., J. Z. Haeggström, and C. C. Leslie. 1996. Lipid mediator networks in cell signaling: update and impact of cytokines. *FASEB J*. 10:1147–1158; Papayianni, A., C. N. Serhan, M. L. Phillips, H. G. Rennke, and H. R. Brady. 1995. Transcellular biosynthesis of lipoxin $A_4$ during adhesion of platelets and neutrophils in experimental immune complex glomerulonephritis. *Kidney Int*. 47:1295–1302). $LXA_4$ is also present in nasal lavage fluids of aspirin-sensitive asthmatics and is generated by leukocytes from patients with asthma and rheumatoid arthritis (Chavis, C., I. Vachier, P. Chanez, J. Bousquet, and P. Godard. 1996. 5(S),15(S)-Dihydroxyeicosatetraenoic acid and lipoxin generation in human polymorphonuclear cells: dual specificity of 5-lipoxygenase towards endogenous and exogenous precursors. *J. Exp. Med*. 183:1633–1643; Thomas, E., J. L. Leroux, F. Blotman, and C. Chavis. 1995. Conversion of endogenous arachidonic acid to 5,15-diHETE and lipoxins by polymorphonuclear cells from patients with rheumatoid arthritis. *Inflamm. Res*. 44:121–124). Like most autacoids and lipid mediators, LX are rapidly biosynthesized, act within a local microenvironment, and are rapidly enzymatically inactivated. To advance the understanding of LX and ATL roles in vivo, metabolically stable LX analogs were designed that resist rapid inactivation and mimic the in vitro actions of naturally occurring LX and ATL (Serhan, C. N., J. F. Maddox, N. A. Petasis, I. Akritopoulou-Zanze, A. Papayianni, H. R. Brady, S. P. Colgan, and J. L. Madara. 1995. Design of lipoxin $A_4$ stable analogs that block transmigration and adhesion of human neutrophils. *Biochemistry* 34:14609–14615). It has been unexpectedly discovered that these compounds are potent inhibitors of TNFα-driven PMN-associated inflammatory events in vitro as well as in vivo. Moreover, $LXA_4$-ATL inhibit MIP-2 and IL-1β yet stimulate the local appearance of IL-4 within exudates.

The present invention pertains to methods for modulating a disease or condition associated with TNFα initiated polymorphoneutrophil (PMN) inflammation. The methods include administration to a subject, an effective anti-inflammatory amount of a lipoxin analog having the formula described infra, such that the TNFα initated PMN inflammation is modulated.

The present invention also pertains to methods for treating TNFα initiated polymorphoneutrophil (PMN) inflammation in a subject. The methods include administration of an effective anti-inflammatory amount of a lipoxin analog described infra, such that TNFα initiated polymorphoneutrophil (PMN) inflammation is treated.

The present invention further pertains to methods for modulating a disease or condition associated with TNFα initiated cytokine activity in a subject. The methods include, administration of an effective anti-TNFα amount of a lipoxin analog described infra, such that a disease or condition associated with TNFα initiated cytokine activity, is modulated.

The present invention further relates to methods for treating TNFα initiated cytokine activity in a subject. The methods include administration of an effective anti-inflammatory amount of a lipoxin analog described infra, such that TNFα initiated cytokine activity, e.g., inflammation, is treated.

The present invention also relates to methods for modulating a disease or condition associated with TNFα initiated IL-1β activity in a subject. The methods include administration of an effective anti-TNFα amount of a lipoxin analog described infra, such that a disease or condition associated with TNFα initiated IL-1β, is modulated.

The present invention further pertains to methods for treating TNFα initiated IL-1β activity in a subject. The methods include administration of an effective anti-TNFα amount of a lipoxin analog described infra, such that TNFα initiated IL-1β activity, e.g., inflammation, is treated.

In preferred embodiments, the methods of the invention are performed in vitro or in vivo.

In another aspect, the present invention is directed to a packaged pharmaceutical composition for treating a the activity or conditions listed above in a subject. The packaged pharmaceutical composition includes a container holding a therapeutically effective amount of at least one lipoxin compound having one of the formulae described infra and instructions for using the lipoxin compound for treating the activity or condition in the subject.

In one embodiment, compounds useful in the invention have the formula (I)

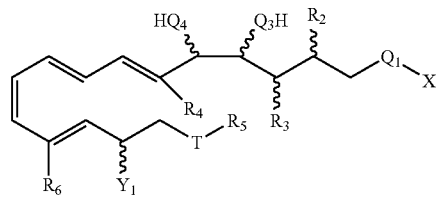

wherein X is $R_1$, $OR_1$, or $SR_1$;
wherein $R_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

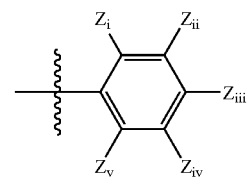

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
  (a) H;
  (b) an alkyl of 1 to 8 carbon atoms, inclusive, which may be a straight chain or branched;
  (c) a cycloalkyl of 3 to 6 carbon atoms, inclusive;
  (d) an alkenyl of 2 to 8 carbon atoms, inclusive, which may be straight chain or branched; or (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

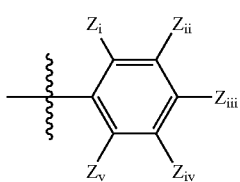

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is (a) H;

(b) an alkyl from 1 to 4 carbon atoms, inclusive, straight chain or branched;

wherein T is O or S, and pharmaceutically acceptable salts thereof.

In another embodiment, compounds useful in the invention have the formula (II)

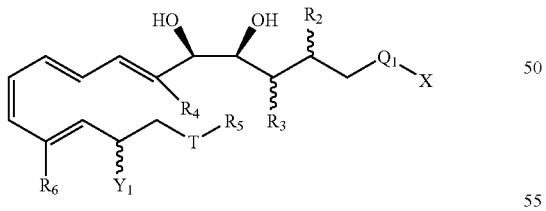

wherein X is $R_1$, $OR_1$, or $SR_1$;

wherein $R_1$ is (i) a hydrogen atom;

(ii) an alkyl of 1 to 8 carbons atoms, inclusive, which may be straight chain or branched;

(iii) a cycloalkyl of 3 to 10 carbon atoms;

(iv) an aralkyl of 7 to 12 carbon atoms;

(v) phenyl;

(vi) substituted phenyl

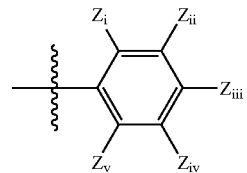

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is (a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

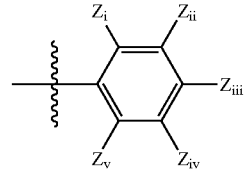

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is (a) H;

(b) an alkyl from 1 to 4 carbon atoms, inclusive, straight chain or branched;

wherein T is O or S, and pharmaceutically acceptable salts thereof.

The invention is also directed to useful lipoxin compounds having the formula (III)

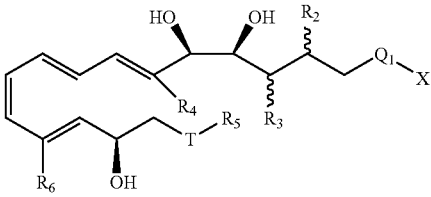

wherein X is $R_1$, $OR_1$, or $SR_1$;

wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

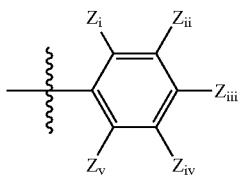

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$, wherein $Q_2$ is $-O-$ or $-S-$; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;

wherein $R_5$ is

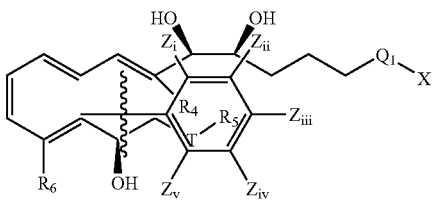

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;

wherein T is O or S, and pharmaceutically acceptable salts thereof.

The invention is further directed to useful lipoxin compounds having the formula (IV)

wherein X is $R_1$, $OR_1$, or $SR_1$;

wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

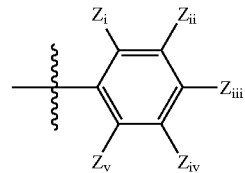

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $Q_1$ is (C=O), $SO_2$ or (CN), provided when $Q_1$ is CN, then X is absent;

wherein $R_4$ is
(a) H;
(b) an alkyl of 1 to 6 carbon atoms, inclusive, which may be a straight chain or branched;

wherein $R_5$ is

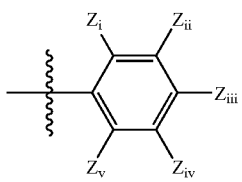

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;

wherein T is O or S, and pharmaceutically acceptable salts thereof.

The invention is further directed to useful lipoxin compounds having the formula (V)

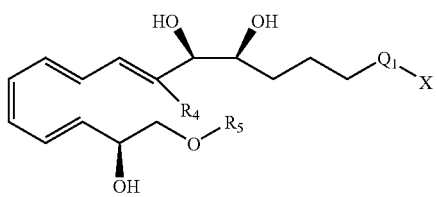

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

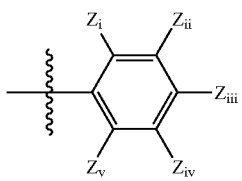

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $R_4$ is
(a) H;
(b) an alkyl of 1 to 6 carbon atoms, inclusive, which may be a straight chain or branched;

wherein $R_5$ is

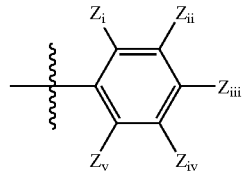

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched; and pharmaceutically acceptable salts thereof.

In preferred embodiments, X is $OR_1$, wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

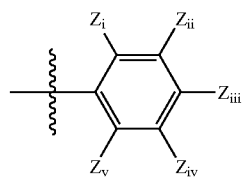

wherein $Z_i$, $Z_{ii}$, $Z_{iii}$, $Z_{iv}$, and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl. In certain embodiments for $R_5$, para-fluorophenyl and unsubstituted phenyl are excluded, e.g., 15-epi-16-(para-fluoro)-phenoxy-$LXA_4$, 15-epi-16-phenoxy-$LXA_4$, 16-(para-fluoro)-phenoxyl-$LXA_4$, and/or 16-phenoxy-$LXA_4$. The compounds encompassed by U.S. Pat. No. 5,441,951 are excluded from certain aspects of the present invention.

In preferred embodiments, $Y_1$ is a hydroxyl and the carbon bearing the hydroxyl can have an R or S configuration. In most preferred embodiments, the chiral carbon bearing the hydroxyl group, e.g., $Y_1$, is designated as a 15-epi-lipoxin as is known in the art.

In certain embodiments the chirality of the carbons bearing the $R_2$, $R_3$, $Q_3$ and $Q_4$ groups can each independently be either R or S. In preferred embodiments, $Q_3$ and $Q_4$ have the chiralities shown in structures II, III, IV or V.

In preferred embodiments, $R_4$ is a hydrogen. In other preferred embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds useful in the present invention can be prepared by the following synthetic scheme:

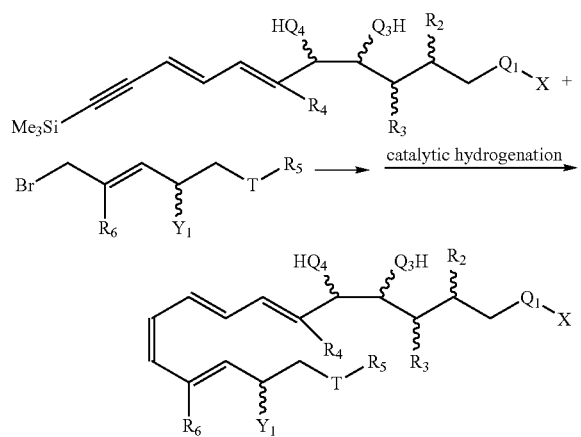

wherein X, $Q_1$, $Q_3$, $Q_4$, $R_2$, $R_3$, $R_4$, $R_5$, $R_6$, $Y_1$ and T are as defined above. Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263.

In still another aspect, the present invention is directed to pharmaceutical compositions including compounds having the above-described formulae and a pharmaceutically acceptable carrier. In one embodiment, a preferred compound is

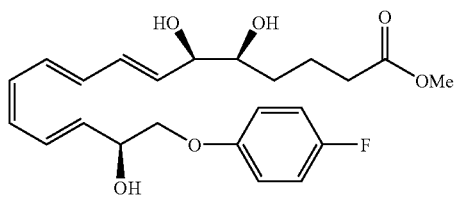

In a preferred embodiment, the pharmaceutical carrier is not a ketone, e.g., acetone.

In one embodiment, the antiinflammatories of the invention can be incorporated into a shampoo or a body cleansing product, e.g., a soap, for cleansing of the scalp and/or body. The use of these compounds in a shampoo or soap product can be used to treat psoriasis, seborrheic dermatitis, pustular dermatosis and dandruff. Thus the compounds are useful for modulating TNF αPMN or cytokine inflammation associated with such conditions.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as a leukotriene), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Preferred lipoxin $A_4$ analogs have an active region comprising $C_5$–$C_{15}$ of natural lipoxin $A_4$. Preferred lipoxin $B_4$ analogs have an active region comprising C5–C14 of natural lipoxin B4.

The term "recognition site" or receptor is art-recognized and is intended to refer generally to a functional macromolecule or complex of macromolecules with which certain groups of cellular messengers, such as hormones, leukotrienes, and lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled lipoxin analog" is further understood to encompass compounds which are labeled with radioactive isotopes, such as but not limited to tritium ($^3H$), deuterium ($^2H$), carbon ($^{14}C$), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native lipoxin. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite.

The term "resists metabolism" is meant to include failing to undergo one or more of the metabolic degradative transformations by at least one of the enzymes which metabolize lipoxins. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo. In certain aspects, the compounds of the invention do not include halogenated compounds, e.g., fluorinated compounds.

The term "subject" is intended to include living organisms susceptible to conditions or diseases caused or contributed to by inflammation, inflammatory responses, vasoconstriction, and myeloid suppression. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiment, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters. In a preferred embodiment, the ester is not a methyl ester (See, for example, Berge et al., supra.).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 per cent to about ninety-nine percent of active ingredient, preferably from about 5 percent to about 70 percent, most preferably from about 10 per cent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension, in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Materials and Methods

Human and mouse recombinant TNFα and human recombinant GM-CSF were obtained from Boehringer Mannheim (Indianapolis, Ind.). Dulbecco's PBS ($Mg^{++}$ and $Ca^{++}$-free), RPMI-1640 and FCS were purchased from Bio Whittaker Inc. (Walkersville, Md.). Ficoll-Hypaque was from Organon Teknika Corp. (Durham, N.C.) and Hank's balanced salt solution was purchased from Gibco BRL (Grand Island, N.Y.). Serum bovine albumin, dextran, antibiotics, L-glutamine, cytochrome C, superoxide dismutase and zymosan were obtained from Sigma (St. Louis, Mo.). The assessment of human IL-1β in supernatants was performed by using an immunometric assay with acetylcholine esterase (Cayman Chemical, Ann Arbor, Mich.). Murine IL-1β was assessed using an ELISA from Endogen (Woburn, Mass.). ELISAs for IL-4 and IL-10 were from Amersham (Arlington Heights, Ill.); MIP-2 and IL-13 ELISAs were from R&D Systems (Minneapolis, Minn.). $LXA_4$ and ATL metabolically stable analogs were prepared and characterized, including nuclear magnetic resonance spectroscopy, as in (14). Concentrations of each LX analog were determined using an extinction coefficient of 50,000 $M^{-1}.cm^{-1}$ just prior to each experiment. Where indicated, statistical analyses were performed using Student's non-paired t-test (two-tailed), and significance (*) was considered to be attained when P was <0.05.

Preparation of Human PMN Suspensions and Superoxide-anion Generation

Venous blood from healthy donors was collected using sterile conditions using acid citrate dextrose (ACD) as an anticoagulant, and PMN were isolated as in (15). PMN were suspended in cold (4° C.) Hank's medium (supplemented with 1.6 mM $Ca^{++}$, 0.1% FCS, 2 mM L-glutamine, 1% penicillin, and 2% streptomycin, pH 7.4). Cell preparations were >98% PMN as determined by Giemsa-Wright staining; cell viability was >98% as determined by trypan blue exclusion and light microscopy. To examine superoxide production, PMN ($1.0 \times 10^6$/ml) were placed at 37° C. (3 min) and then exposed to either vehicle (0.1% ethanol) or synthetic $LXA_4$, 15R/S-methyl $LXA_4$ or 16-phenoxy-$LXA_4$ for 5 min at 37° C. Before adding TNFα (50 ng/ml), PMN were incubated with cytochrome C (0.7 mg/ml) for 10 min at 37° C. Superoxide dismutase-dependent reduction of cytochrome C was terminated by rapidly placing tubes in an ice-water bath. The extent of cytochrome C reduction in each supernatant was determined at 550 nm in reference to control values obtained when superoxide dismutase was added before a stimulus or vehicle control. Cytochrome C reduction was quantitated using the extinction coefficient of 21.1/mmol/L.

RNA Isolation and Northern Blot Analysis

Total RNA extraction and Northern blot analyses were performed as in (7). pSM320 vector containing cDNA for IL-1β was purchased from ATCC.

Murine Air Pouches

Six to eight week old male BALB/c mice were obtained from Taconic Farms (Germantown, N.Y.). Air pouches were raised on the dorsum by s.c. injection of 3 ml of sterile air on day 0 and day 3. All experiments were conducted on day 6 (16). Individual air pouches (one per mouse) were injected with either vehicle alone (0.1% ethanol), TNFα, 15 R/S-methyl-$LXA_4$ or TNFα plus 15 R/S-methyl-$LXA_4$, and each was suspended in 1 ml endotoxin-free PBS immediately before injection into pouch cavities. At given intervals, the mice were sacrificed and individual air pouches were lavaged three times with sterile PBS (1 ml). The exudates were centrifuged at 2000 RPM (5 min) and the supernatants were removed. Cell pellets were suspended in PBS (200 μl) for enumeration and assessed for viability. Fifty μl of each cell suspension was mixed with 150 μl 30% BSA and then centrifuged onto microscope slides at 500 RPM for 5 min using a cytospin centrifuge, air dried, and stained with Giemsa-Wright.

Inhibition of TNFα-stimulated Superoxide Generation

TNFα, although a modest agonist of $O_2^-$ generation by human PMN, is a physiologically relevant stimulus for the generation of reactive oxygen species (ROS) by human PMN that can play critical roles in local tissue injury during both inflammation and reperfusion (Tsujii, M., S. Kawano, S. Tsuji, H. Sawaoka, M. Hori, and R. N. DuBois. 1998. Cyclooxygenase regulates angiogenesis induced by colon cancer cells. Cell 93:705–716; Shibuya, H., N. Ohkohchi, S. Tsukamoto, and S. Satomi. 1997. Tumor necrosis factor-induced, superoxide-mediated neutrophil accumulation in cold ischemic/reperfused rat liver. Hepatology 26:113–120; Jaeschke, H., A. Farhood, and C. W. Smith. 1990. Neutrophils contribute to ischemia/reperfusion injury in rat liver in vivo. FASEB J. 4:3355–3359). In FIG. 1, the impact of $LXA_4$ and ATL related bioactive stable analogs were evaluated on TNFα stimulated superoxide anion production. Native $LXA_4$ and the analogs (15 R/S-methyl-$LXA_4$ and 16 phenoxy-$LXA_4$) inhibited TNFα-stimulated superoxide anion generation in a concentration-dependent fashion. Their rank order of potency at 10 nM was 15 R/S-methyl-$LXA_4$ (81.3±14.1% inhibition)>>16 phenoxy-$LXA_4$ (93.7±3.2%)>$LXA_4$ (34.3±2.3%). 15R/S-methyl-$LXA_4$ covers both $LXA_4$ and ATL in structure, and 16-phenoxy-$LXA_4$ is a $LXA_4$ analog (see FIG. 1). Each analog competes at the $LXA_4$ receptor. (Takano, T., S. Fiore, J. F. Maddox, H. R. Brady, N. A. Petasis, and C. N. Serhan. 1997. Aspirin-triggered 15-epi-lipoxin $A_4$ and $LXA_4$ stable analogs are potent inhibitors of acute inflammation: Evidence for anti-inflammatory receptors. J. Exp. Med. 185:1693–1704). Neither $LXA_4$, 15 R/S-methyl-$LXA_4$ nor 16 phenoxy-$LXA_4$, at concentrations up to 1000 nM added to cells alone, stimulated generation of ROS. 15 R/S-methyl-$LXA_4$ and 16 phenoxy-$LXA_4$ were approximately three times more potent than native LXA$_4$ and proved to be powerful inhibitors of TNFα-stimulated superoxide generation by PMN. However, neither LXA$_4$ nor its analogs inhibit PMA (100 nM; n=3; not shown) or fMLP-stimulated O$_2^-$ production. Inhibition of ROS by LXA$_4$ and its analogs is of interest in a context of ischemia/reperfusion, where ROS are held to be primary mediators of tissue injury (15).

Suppression of TNFα-stimulated IL-1β Release

Figure 2A:
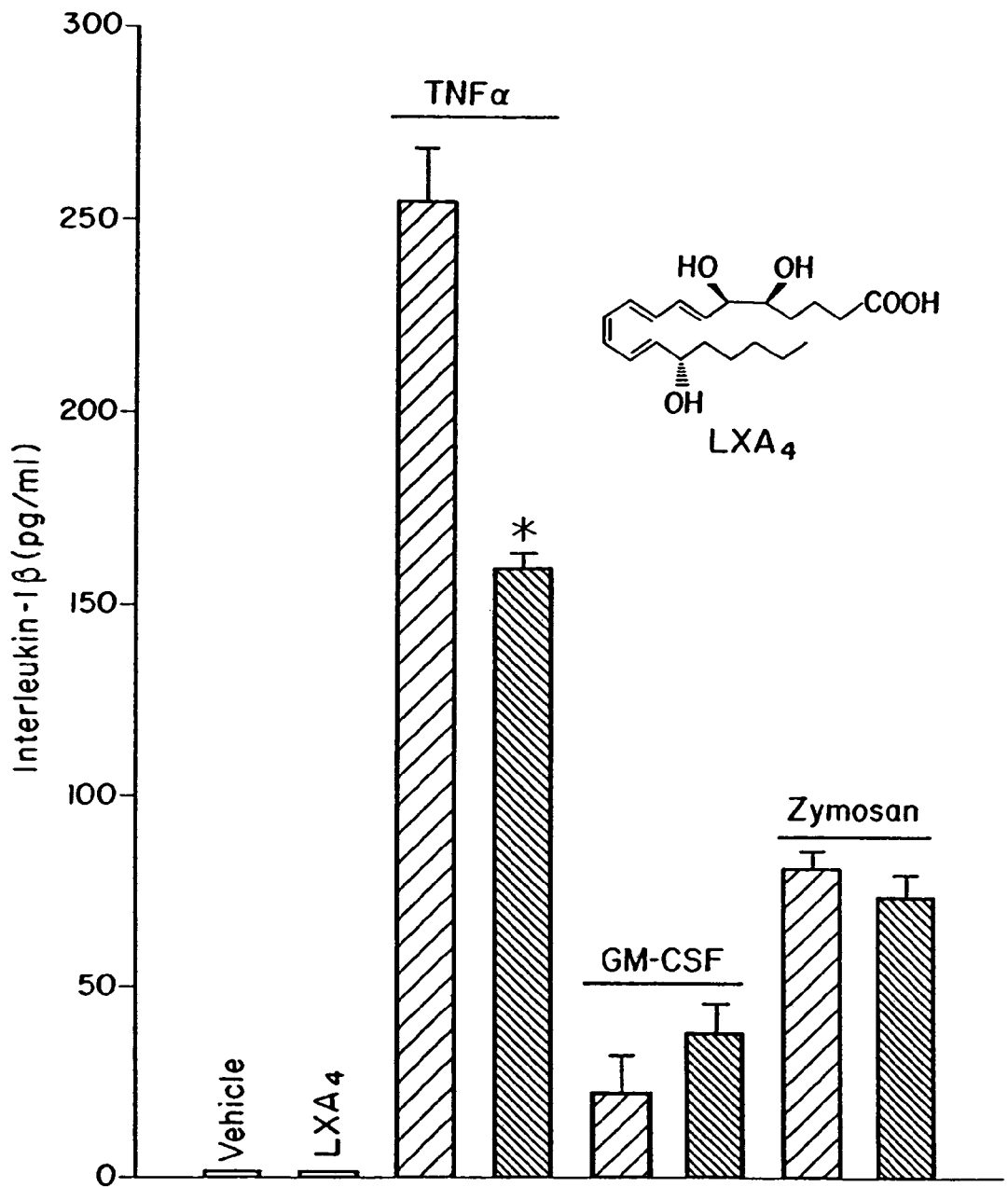
FIGS. 2A and 2B show that $LXA_4$ and stable analogs inhibit TNFα-induced IL-1β production in human neutrophils. A) PMN were incubated (TNFα (10 ng/ml) plus vehicle or TNFα plus LXA$_4$ (100 nM)) as denoted for 20 h at 37° C. and 5% CO$_2$. Supernatants were collected, and IL-1β was quantitated by ELISA. Results are expressed as mean±SD of duplicates, and are from one experiment representative of n=3. B) PMN were incubated for indicated periods of time in the presence of increasing concentrations of 15 R/S-methyl-LXA$_4$. Values represent the mean±SEM, n=3. At all time intervals tested, TNFα induced a significant appearance of IL-1β over vehicle-treated cells (*p<0.01).

PMN express and release interleukin-1β, which is a potent proinflammatory cytokine (Dinarello, C. A. 1996. Biologic basis for interleukin-1 in disease. *Blood* 87:2095–2147). Therefore, the actions of native LXA$_4$ and its analogs on TNFα-induced IL-1β release were investigated. Incubation of PMN with physiologically relevant concentrations of TNFα, GM-CSF or phagocytic particles (zymosan) resulted in a concentration dependent increase in the levels of IL-1β present in supernatants. Approximate EC$_{50}$ for each agonist were: TNFα, 10 ng/ml; GM-CSF, 10 U/ml; and zymosan, 100 µg/ml. Native LXA$_4$ specifically inhibited TNFα-induced IL-1β release (FIG. 2A), while similar amounts of IL-1β were released in the presence or absence of LXA$_4$ when PMN were exposed to either GM-CSF or zymosan.

Figure 2B:
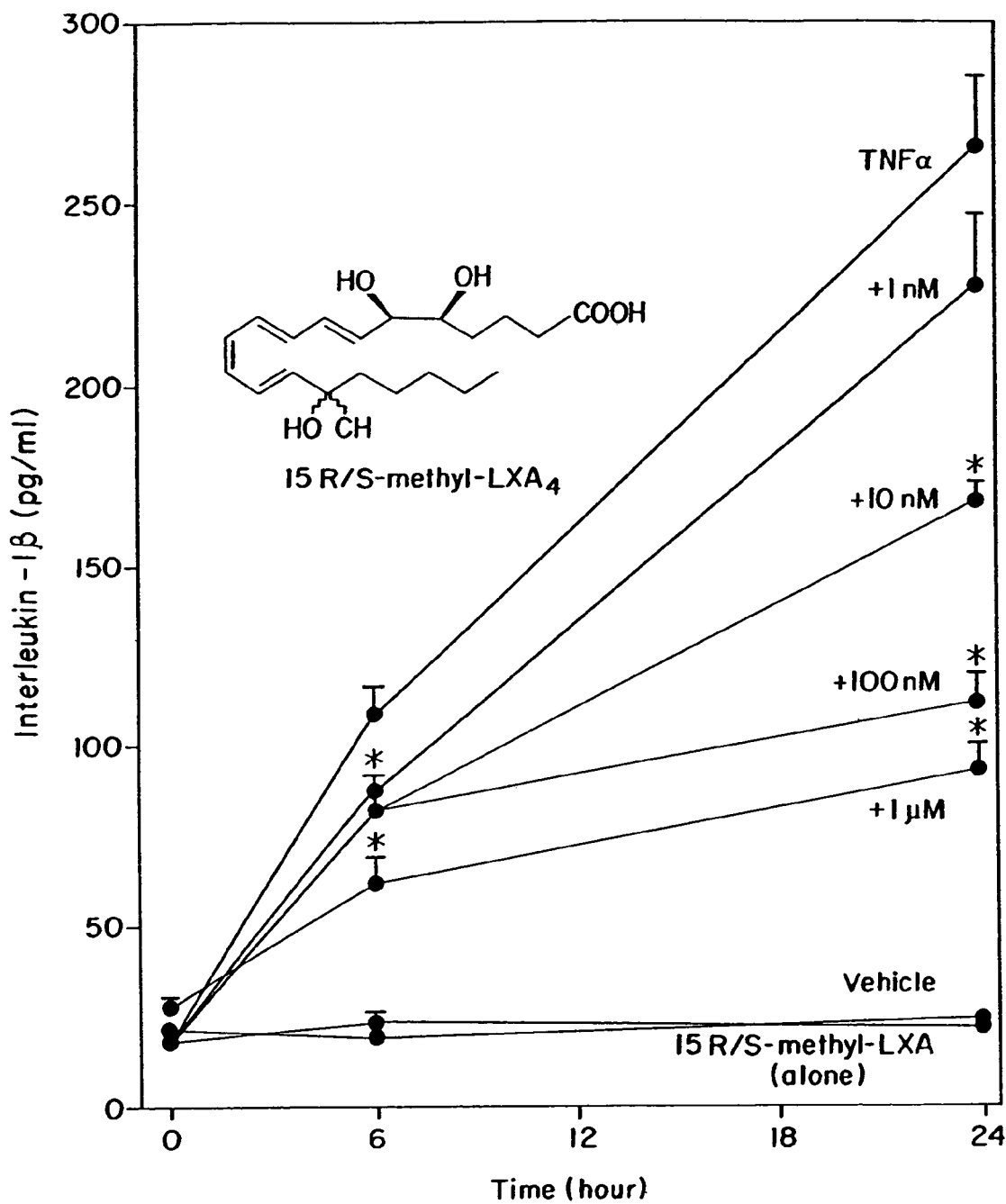
Figure 3:
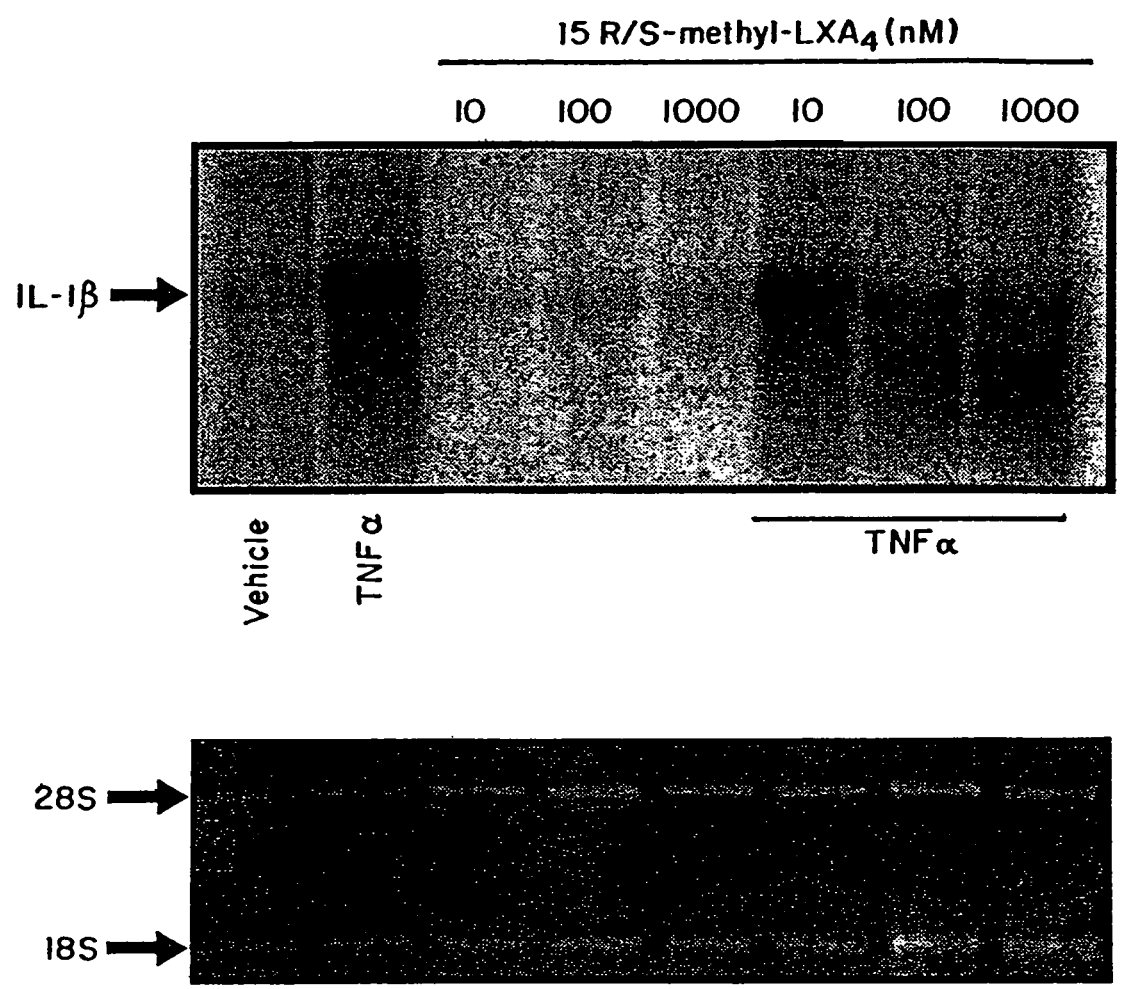
FIG. 3 demonstrates 15 R/S-methyl-LXA$_4$ downregulates TNFα-triggered IL-1β gene expression. PMN were incubated with either 0.1% ethanol (vehicle) or 15 R/S-methyl-LXA$_4$ at 10, 100, and 1000 nM, in the presence or absence of TNFα (10 ng/ml), for 6 h at 37° C. Northern blots were performed in order to detect IL-1β messenger RNA. The results presented are from one experiment which is representative of two others performed with different donors.

PMN were exposed to increasing concentrations of 15 R/S-methyl-LXA$_4$, 16-phenoxy-LXA$_4$ or native LXA$_4$ in the presence of TNFα (10 ng/ml) or vehicle alone. At a concentration of 100 nM, 15 R/S-methyl-LXA$_4$ inhibited~60% of IL-1β release, and 16-phenoxy-LXA$_4$ at equimolar levels gave approximately 40% inhibition (values comparable to those obtained with native LXA$_4$). Time course and concentration dependence were carried out with 15 R/S-methyl LXA$_4$ (FIG. 2B). At 10 nM, 15 R/S-methyl-LXA$_4$ gave clear statistically significant inhibition, which was evident within 6 h and more prominent after 24 h (FIG. 2B). Inhibition of IL-1β by these LX analogs was, at least in part, the result of a down-regulation in gene expression, since the IL-1β messenger RNA levels in cells treated with TNFα (10 ng/ml) plus 15 R/S-methyl-LXA$_4$ (100 nM) were decreased by approximately 60% when compared to cells treated with TNFα alone (FIG. 3). Therefore, since IL-1β and TNFα are two cytokines that are considered important in inflammation, the inhibition of IL-1β observed (FIGS. 1 & 2) suggested that 15 R/S-methyl-LXA$_4$ might exert a potent in vivo anti-cytokine action (vide infra).

Involvement of LXA$_4$ Receptor

Figure 4:
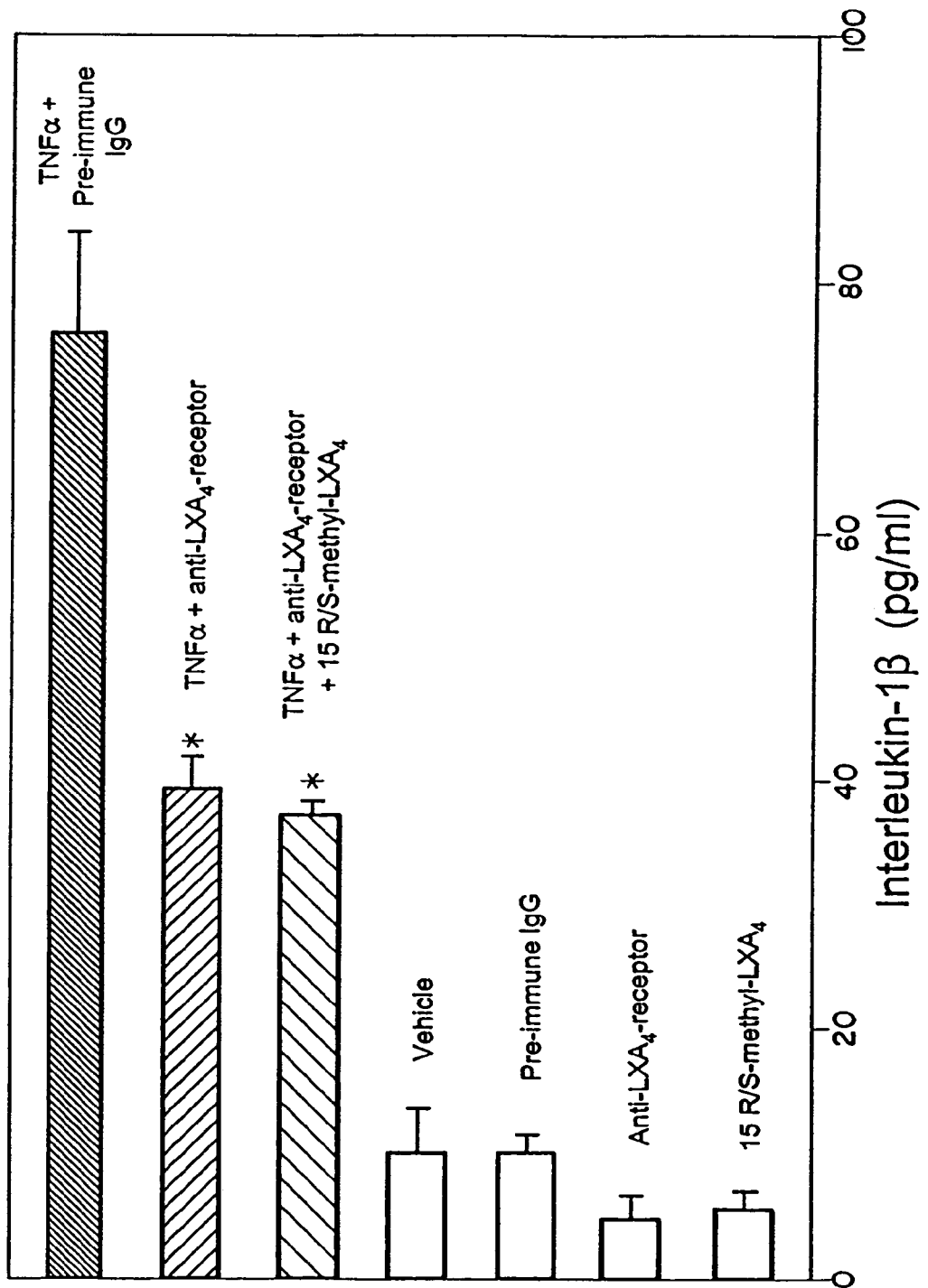
FIG. 4 depicts the involvement of the LXA$_4$ receptor. PMN were incubated with either IgG purified from preimmune serum (50 µg/ml) or anti-LXA$_4$ receptor (50 µg/ml) for 1 h at 4° C., then exposed to agonists for 12 h at 37° C. and 5% CO$_2$. Values are expressed as mean±SD from an experiment performed in triplicate, which is representative of three distinct experiments each performed with different donors (*p<0.1).

To investigate whether the LXA$_4$ receptor (LXA$_4$-R) was involved in the regulation of TNFα-stimulated IL-1β release, the rabbit polyclonal antibodies against a portion of the third extracellular domain (ASWGGTPEERLK) of LXA$_4$-R prepared earlier were used (Fiore, S., and C. N. Serhan. 1995. Lipoxin A$_4$ receptor activation is distinct from that of the formyl peptide receptor in myeloid cells: inhibition of CD11/18 expression by lipoxin A$_4$-lipoxin A$_4$ receptor interaction. *Biochemistry* 34:16678–16686). PMN were incubated with ~50 µg/ml of either preimmune protein-A purified IgG or IgG directed against LXA$_4$-R for 1 h at 4° C. prior to exposure to TNFα (10 ng/ml) and 15 R/S-methyl-LXA$_4$ (100 nM). Anti-LXA$_4$-R antibodies prevented IL-1β release by TNFα, suggesting that the third extracellular loop plays a crucial role in LXA$_4$ receptor activation (FIG. 4). 15 R/S-methyl-LXA$_4$ inhibited about 50% of IL-1β release. When added together, anti-LXA$_4$-R antibodies and 15R/S-methyl-LXA$_4$ in the presence of TNFα did not further inhibit IL-1β appearance, and neither anti-LXA$_4$-R antibodies nor 15 R/S-LXA$_4$ alone stimulated significant amounts of IL-1β to appear within supernatants. The results of these experiments are two fold: first, they indicated that the inhibitory action of 15 R/S-methyl-LXA$_4$ is transduced via the LXA$_4$ receptor and second, that the anti-LXA$_4$-R antibodies alone activate the LXA$_4$ receptor and lead to inhibition of IL-1β release.

Inhibition of TNFα-directed Leukocyte Trafficking In Vivo

Figure 5:
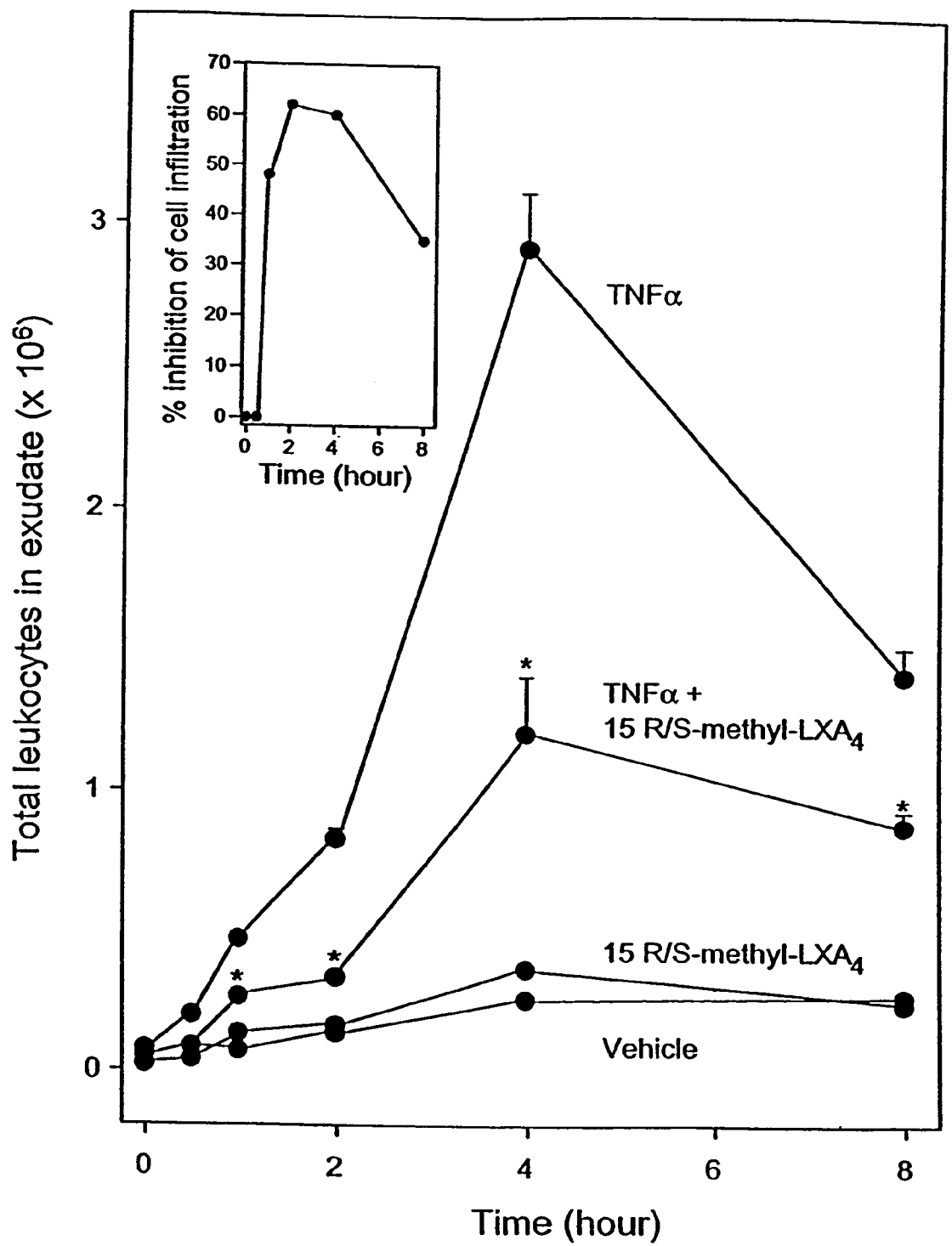
FIG. 5 shows the inhibition of TNFα-induced PMN infiltration in murine air pouches. One ml of sterile PBS containing either 0.1% ethanol, TNFα, 15 R/S-methyl-LXA$_4$, or TNFα plus 15 R/S-methyl-LXA$_4$ was injected into the pouches, and the exudates were collected at indicated time periods. The total number of leukocytes was counted as in *Materials & Methods*. The results are expressed as mean±SEM from three different mice for each point. At all time intervals, TNFα induced a significant leukocyte infiltration into the air pouch cavity (P<0.05). *Statistically different from TNFα-treated cells; and from vehicle- or 15 R/S-methyl-LXA$_4$-treated cells (p<0.01).

Since TNFα evokes leukocyte infiltration in a chemokine-dependent fashion in the murine six day air pouch, the impact of 15 R/S-methyl-LXA$_4$ in this model was evaluated to determine whether LXA$_4$ or ATL also intersects the cytokine-chemokine axis in vivo (Tessier, P. A., P. H. Naccache, I. Clark-Lewis, R. P. Gladue, K. S. Neote, and S. R. McColl. 1997. Chemokine networks in vivo: involvement of C-X-C and C—C chemokines in neutrophil extravasation in vivo in response to TNF-α. *J. Immunol.* 159:3595–3602; Sin, Y. M., A. D. Sedgwick, E. P. Chea, and D. A. Willoughby. 1986. Mast cells in newly formed lining tissue during acute inflammation: a six day air pouch model in the mouse. *Ann. Rheum. Dis.* 45:873–877). 15 R/S-methyl-LXA$_4$ is the most subtle modification to native LXA$_4$ and ATL structure with addition of a methyl at carbon 15. Murine TNFα (10 ng/ml) caused a transient infiltration of leukocytes to the air pouch in a time-dependent fashion with maximal accumulation at 4 h. 15 R/S-methyl-LXA$_4$ at 25 nmoles inhibited the TNFα-stimulated recruitment of leukocytes to the air pouch by 62% (FIG. 5). Inhibition was evident at 1 h, and maximal between 2 h and 4 h. At these intervals, a more than 60% reduction in leukocyte infiltration was noted that remained significantly reduced at 8 h (FIG. 5, insert). Injection of pouches with either vehicle or the analog alone did not cause a significant leukocyte infiltration. Also, inflammatory exudates were collected 4 h after injection with vehicle alone, TNFα, 15 R/S-methyl-LXA$_4$ alone, or TNFα plus 15 R/S-methyl-LXA$_4$, and cell types were enumerated. In the six-day pouches given TNFα, PMN constituted the major cell type present within the exudates at 4 h and ranged from 80 to 85% of total cell number. Administration of both 15 R/S-methyl-LXA$_4$ and TNFα into the six day air pouch cavity inhibited migration of PMN and eosinophils/basophils as well as mononuclear cells (Table I). Of interest, administration of 15 R/S-methyl-LXA$_4$ alone evoked a small but statistically significant increase in mononuclear cell influx (Table I), a result which is consistent with earlier in vitro observations in which specific stimulation of monocyte and inhibition of PMN chemotaxis have been observed (Maddox, J. F., M. Hachicha, T. Takano, N. A. Petasis, V. V. Fokin, and C. N. Serhan. 1997. Lipoxin A$_4$ stable analogs are potent mimetics that stimulate human monocytes and THP-1 cells via a G-protein linked lipoxin A$_4$ receptor. *J. Biol. Chem.* 272:6972–6978).

TABLE I

TNFα-induced leukocyte infiltration in murine air pouches: Inhibitory action of 15 R/S-methyl-LXA$_4$†.

| | Number of leukocytes present in the pouch (x10$^6$) | | |
|---|---|---|---|
| Injection | Neutrophils | Eosinophils/ Basophils | Monocytes/ Macrophages |
| TNFα | 2.40 ± 0.10* | 0.30 ± 0.01* | 0.20 ± 0.01* |
| 15 R/S-methyl-LXA$_4$ + TNFα | 0.98 ± 0.10** (59.1%) | 0.13 ± 0.01** (56.0%) | 0.10 ± 0.01** (50%) |

TABLE I-continued

TNFα-induced leukocyte infiltration in murine air pouches:
Inhibitory action of 15 R/S-methyl-LXA$_4$†.

| | Number of leukocytes present in the pouch (×10$^6$) | | |
|---|---|---|---|
| Injection | Neutrophils | Eosinophils/ Basophils | Monocytes/ Macrophages |
| 15 R/S-methyl-LXA$_4$ | 0.25 ± 0.01 | 0.03 ± 0.01 | 0.14 ± 0.01* |
| Vehicle | 0.30 ± 0.01 | 0.07 ± 0.01 | 0.06 ± 0.01 |

†Air pouches were raised as described in Materials and Methods. Each mouse was injected with 1 ml PBS containing either vehicle (0.1% ethanol), TNFα (10 ng), 15 R/S-methyl-LXA$_4$ (25 nmoles) or TNFα plus 15 R/S-methyl-LXA$_4$. Leukocyte infiltration was determined 4 h post-injection.
Results present the mean ± SEM of three different mice. Percent inhibition is indicated in parentheses. Statistically different from
*vehicle-injected mice ($p < 0.01$), and from
**TNFα-injected mice ($p < 0.01$).

Cytokine-chemokine Profiles

Since MIP-2 is the major chemokine involved in recruiting PMN to the air pouch following injection of TNFα, the action of 15 R/S-methyl-LXA$_4$ in this TNFα-induced chemokine/cytokine axis was determined. MIP-2 and IL-1β are important pro-inflammatory cytokines, and IL-4, IL-10 and IL-13 possess immunomodulatory properties (Isomaki, P., and J. Punnonen. 1997. Pro- and anti-inflammatory cytokines in rheumatoid arthritis. *Ann. Med.* 29:499–507; Volpert, O. V., T. Fong, A. E. Koch, J. D. Peterson, C. Waltenbaugh, R. I. Tepper, and N. P. Bouck. 1998. Inhibition of angiogenesis by interleukin 4. *J. Exp. Med.* 188:1039–1046). Exudates from selected time intervals were collected and cell-free supernatants assessed for the presence of these murine cytokines. TNFα induced maximal detectable amounts of MIP-2 and ILW-1β within 90 minutes (not shown). 15 R/S-methyl-LXA$_4$ (25 nmoles) inhibited TNFα-stimulated MIP-2 and IL-1β release by 48% and 30% respectively (FIG. 6). 15 R/S-methyl-LXA$_4$ alone in the air pouch did not stimulate MIP-2 or IL-1β release. In sharp contrast, 15 R/S-methyl-LXA$_4$ stimulated the appearance of IL-4 within the exudates. This stimulation of IL-4 was observed both in the absence as well as presence of TNFα. Neither IL-10 nor IL-13 was detected within the pouch exudates. These results demonstrate that administration of 15 R/S-methyl-LXA$_4$ modified the cytokine-chemokine axis in TNFα-initiated acute inflammation, and of interest this re-orientation of the cytokine-chemokine axis paralleled the reduction in leukocyte infiltration.

Figure 6:
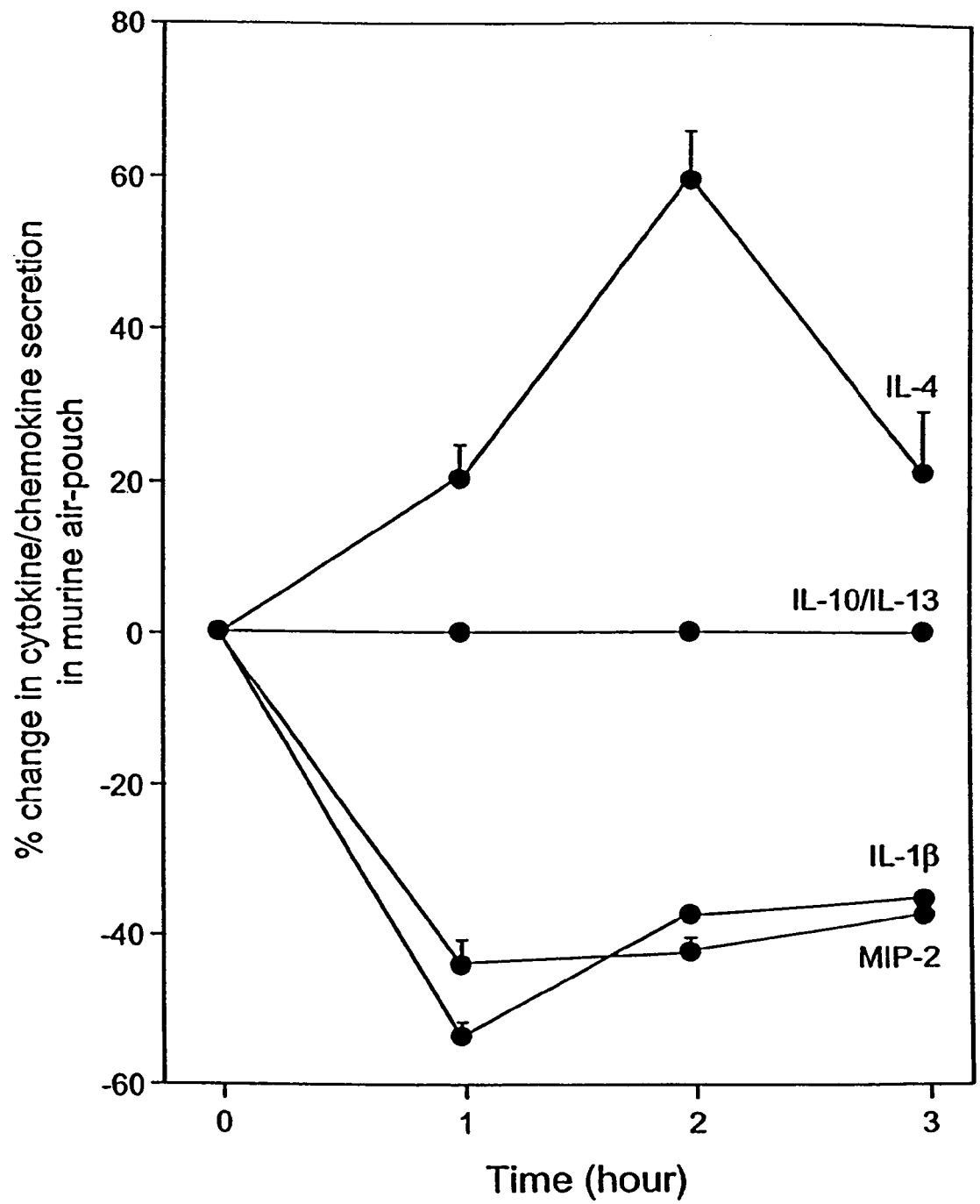
FIG. 6 shows that 15 R/S-methyl-LXA$_4$ redirects the TNFα-induced cytokine/chemokine profile in vivo. Experiments were conducted as described in FIG. 5 legend. Quantitation for IL-1β, IL-4, IL-10, IL-13 and MIP-2 was performed using ELISA with air pouch cell-free exudates. The results are expressed as mean±SEM from three different mice for each point. Changes in IL-1β, MIP-2 and IL-4 were significant at all tested time intervals (p<0.01).

Several different strategies have been explored in an attempt to attenuate nondesirable action of TNFα in inflammatory diseases and ischemia/reperfusion injury including treatment of patients suffering from rheumatoid arthritis with specific Fc portion of monoclonal antibodies directed against TNFα-receptor (26). Different steroidal and nonsteroidal drugs to alleviate the pain and the severity of inflammatory responses are extensively used (Marriott, J. B., M. Westby, and A. G. Dalgleish. 1997. Therapeutic potential of TNF-α inhibitors old and new. *DDT* 2:273–282). However, certain clinical settings such as reperfusion injury are still not well controlled, and new therapeutic agents are needed. The present results indicate that LXA$_4$ and ATL, as evidenced by the actions of their metabolically stable analogs (16-phenoxy-LXA$_4$ and 15 R/S-methyl-LXA$_4$), are potent cytokine-regulating lipid mediators that can also impact the course of inflammation initiated by TNFα and IL-1β. These two cytokines are considered to be key components in orchestrating the rapid inflammatory-like events in ischemia/reperfusion (within minutes to hours), and are major cytokines in rheumatoid arthritis and many other chronic diseases. Of interest, in an exudate and skin wound model, 15 R/S-methyl-LXA$_4$ not only inhibited the TNFα-elicited appearence of IL-1β and MIP-2, but also concomitantly stimulated IL-4 (FIGS. 5–6). This represents the first observation that lipoxins induce upregulation of a potential "anti-inflammatory" cytokine such as IL-4. Hence, it is of particular interest that IL-4 inhibits PMN influx in acute antibody-mediated inflammation and inhibits H$_2$O$_2$ production by IFNγ-treated human monocytes (Saleem, S., Z. Dai, S. N. Coelho, B. T. Konieczny, K. J. M. Assmann, F. K. Baddoura, and F. G. Lakkis. 1998. IL-4 is an endogenous inhibitor of neutrophil influx and subsequent pathology in acute antibody-mediated inflammation. *J. Immunol.* 160: 979–984; Lehn, M., W. Y. Weiser, S. Engelhorn, S. Gillis, and H. G. Remold. 1989. IL-4 inhibits H$_2$O$_2$ production and antileishmanial capacity of human cultured monocytes mediated by IFN-γ. *J. Immunol.* 143:3020–3024). IL-4 is also an active antitumor agent and most recently was shown to be a potent inhibitor of angiogenesis (Volpert, O. V., T. Fong, A. E. Koch, J. D. Peterson, C. Waltenbaugh, R. I. Tepper, and N. P. Bouck. 1998. Inhibition of angiogenesis by interleukin 4. *J. Exp. Med.* 188:1039–1046). It is thus likely that the increase in IL-4 levels stimulated by metabolically stable LX analogs may mediate in part some of the in vivo impact of LXA$_4$ and aspirin-triggered 15-epi-LXA$_4$, a finding that opens a new understanding of the relationship between "antiinflammatory" cytokines and lipid mediators.

In conclusion, LXA$_4$ and aspirin-triggered-LXA$_4$ appear to be involved in controlling both acute as well as chronic inflammatory responses. The results presented here support the notion that aspirin may exert in part its beneficial action via the biosynthesis of endogenous aspirin-triggered-LXA$_4$ that can in turn act directly on PMN and/or the appearance of IL-4. Thus, LX-ATL can protect host tissues via multilevel regulation of proinflammatory signals.

REFERENCES

1. Serhan, C. N., J. Z. Haeggström, and C. C. Leslie. 1996. Lipid mediator networks in cell signaling: update and impact of cytokines. *FASEB J.* 10:1147–1158.
2. Weiss, S. J. 1989. Tissue destruction by neutrophils. *N. Engl. J. Med.* 320:365–376.
3. Marucha, P. T., R. A. Zeff, and D. L. Kretuzer. Cytokine-induced IL-1β gene expression in the human polymorphonuclear leukocyte: transcriptional and post-transcriptional regulation by tumor necrosis factor and IL-1. *J. Immunol.* 147:2603–2608.
4. Lloyd, A. R., and J. J. Oppenheim. 1992. Poly's lament: the neglected role of the polymorphonuclear neutrophil in the afferent limb of the immune response. *Immunology Today* 13:169–172.
5. Hachicha, M., P. H. Naccache, and S.R. McColl. 1995. Inflammatory microcrystals differentially regulate the secretion of macrophage inflammatory protein-1 and interleukin-8 by human neutrophils: A possible mechanism of neutrophil recruitment to sites of inflammation in synovitis. *J. Exp. Med.* 182:2019–2025.
6. Hansen, P. R. 1995. Role of neutrophils in myocardial ischemia and reperfusion. *Circulation* 91:1872–1885.
7. Takano, T., S. Fiore, J. F. Maddox, H. R. Brady, N. A. Petasis, and C. N. Serhan. 1997. Aspirin-triggered 15-epi-lipoxin A$_4$ and LXA$_4$ stable analogs are potent inhibitors of acute inflammation: Evidence for anti-inflammatory receptors. *J. Exp. Med.* 185:1693–1704.

8. Clària, J., and C. N. Serhan. 1995. Aspirin triggers previously undescribed bioactive eicosanoids by human endothelial cell-leukocyte interactions. *Proc. Natl. Acad. Sci. USA* 92:9475–9479.

9. Lee, T. H., C. E. Horton, U. Kyan-Aung, D. Haskard, A. E. Crea, and B. W. Spur. 1989. Lipoxin $A_4$ and lipoxin $B_4$ inhibit chemotactic responses of human neutrophils stimulated by leukotriene $B_4$ and N-formyl-L-methionyl-L-leucyl-L-phenylalanine. *Clin. Sci.* 77:195–203.

10. Serhan, C. N. 1994. Lipoxin biosynthesis and its impact in inflammatory and vascular events. *Biochim. Biophys. Acta* 1212:1–25.

11. Papayianni, A., C. N. Serhan, M. L. Phillips, H. G. Rennke, and H. R. Brady. 1995. Transcellular biosynthesis of lipoxin $A_4$ during adhesion of platelets and neutrophils in experimental immune complex glomerulonephritis. *Kidney Int.* 47:1295–1302.

12. Chavis, C., I. Vachier, P. Chanez, J. Bousquet, and P. Godard. 1996. 5(S),15(S)-Dihydroxyeicosatetraenoic acid and lipoxin generation in human polymorphonuclear cells: dual specificity of 5-lipoxygenase towards endogenous and exogenous precursors. *J. Exp. Med.* 183:1633–1643.

13. Thomas, E., J. L. Leroux, F. Blotman, and C. Chavis. 1995. Conversion of endogenous arachidonic acid to 5,15-diHETE and lipoxins by polymorphonuclear cells from patients with rheumatoid arthritis. *Inflamm. Res.* 44:121–124.

14. Serhan, C. N., J. F. Maddox, N. A. Petasis, I. Akritopoulou-Zanze, A. Papayianni, H. R. Brady, S. P. Colgan, and J. L. Madara. 1995. Design of lipoxin $A_4$ stable analogs that block transmigration and adhesion of human neutrophils. *Biochemistry* 34:14609–14615.

15. Gronert, K., S. P. Colgan, and C. N. Serhan. 1998. Characterization of human neutrophil and endothelial cell ligand-operated extracellular acidification rate by microphysiometry: impact of reoxygenation. *J. Pharmacol. Exp. Ther.* 285:252–261.

16. Tessier, P. A., P. H. Naccache, I. Clark-Lewis, R. P. Gladue, K. S. Neote, and S. R. McColl. 1997. Chemokine networks in vivo: involvement of C-X-C and C-C chemokines in neutrophil extravasation in vivo in response to TNF-α. *J. Immunol.* 159:3595–3602.

17. Tsujii, M., S. Kawano, S. Tsuji, H. Sawaoka, M. Hori, and R. N. DuBois. 1998. Cyclooxygenase regulates angiogenesis induced by colon cancer cells. *Cell* 93:705–716.

18. Shibuya, H., N. Ohkohchi, S. Tsukamoto, and S. Satomi. 1997. Tumor necrosis factor-induced, superoxide-mediated neutrophil accumulation in cold ischemic/reperfused rat liver. *Hepatology* 26:113–120.

19. Jaeschke, H., A. Farhood, and C. W. Smith. 1990. Neutrophils contribute to ischemia/reperfusion injury in rat liver in vivo. *FASEB J.* 4:3355–3359.

20. Dinarello, C. A. 1996. Biologic basis for interleukin-1 in disease. *Blood* 87:2095–2147.

21. Fiore, S., and C. N. Serhan. 1995. Lipoxin $A_4$ receptor activation is distinct from that of the formyl peptide receptor in myeloid cells: inhibition of CD11/18 expression by lipoxin $A_4$-lipoxin $A_4$ receptor interaction. *Biochemistry* 34:16678–16686.

22. Sin, Y. M., A. D. Sedgwick, E. P. Chea, and D. A. Willoughby. 1986. Mast cells in newly formed lining tissue during acute inflammation: a six day air pouch model in the mouse. *Ann. Rheum. Dis.* 45:873–877.

23. Maddox, J. F., M. Hachicha, T. Takano, N. A. Petasis, V. V. Fokin, and C. N. Serhan. 1997. Lipoxin $A_4$ stable analogs are potent mimetics that stimulate human monocytes and THP-1 cells via a G-protein linked lipoxin $A_4$ receptor. *J. Biol. Chem.* 272:6972–6978.

24. Isomaki, P., and J. Punnonen. 1997. Pro- and anti-inflammatory cytokines in rheumatoid arthritis. *Ann. Med.* 29:499–507.

25. Volpert, O. V., T. Fong, A. E. Koch, J. D. Peterson, C. Waltenbaugh, R. I. Tepper, and N. P. Bouck. 1998. Inhibition of angiogenesis by interleukin 4. *J. Exp. Med.* 188:1039–1046.

26. Moreland, L. W., S. W. Baumgartner, M. H. Schiff, E. A. Tindall, R. M. Fleischmann, A. L. Weaver, R. E. Ettlinger, S. Cohen, W. J. Koopman, K. Mohler, M. B. Widmer, and C. M. Blosch. 1997. Treatment of rehumatoid arthritis with a recombinant human tumor necrosis factor receptor (p75)-Fc fusion protein. *N. Engl. J. Med.* 337:141–147.

27. Marriott, J. B., M. Westby, and A. G. Dalgleish. 1997. Therapeutic potential of TNF-α inhibitors old and new. *DDT* 2:273–282.

28. Saleem, S., Z. Dai, S. N. Coelho, B. T. Konieczny, K. J. M. Assmann, F. K. Baddoura, and F. G. Lakkis. 1998. IL-4 is an endogenous inhibitor of neutrophil influx and subsequent pathology in acute antibody-mediated inflammation. *J. Immunol.* 160:979–984.

29. Lehn, M., W. Y. Weiser, S. Engelhorn, S. Gillis, and H. G. Remold. 1989. IL-4 inhibits $H_2O_2$ production and antileishmanial capacity of human cultured monocytes mediated by IFN-γ. *J. Immunol.* 143:3020–3024.

One having ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. A method for treating TNFα initiated polymorphoneutrophil (PMN) inflammation in a subject, comprising administering to the subject an effective anti-TNFα amount of a lipoxin analog having the formula where X is $R_1$, $OR_1$, $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

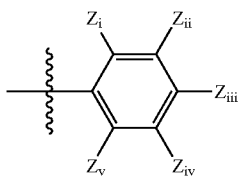

wherein $Z_i$, $Z_{ii}$, $Z_{iii}$, $Z_{iv}$ and $Z_v$, are each independently selected from —$NO_2$, —CN, —C(=O)—$R_T$, —$SO_3H$, a hydrogen atom, halogen, methyl, —$OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;
wherein $R_T$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

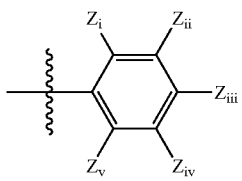

wherein $Z_i$, $Z_{ii}$, $Z_{iii}$, $Z_{iv}$ and $Z_v$, are each independently selected from —$NO_2$, —CN, —$SO_3H$, a hydrogen atom, halogen, methyl, —$OR_x$, wherein $R_x$ is 1 to 8 carbon atoms, inclusive, which may be a straight chain or branched, and hydroxyl;
wherein $Q_1$ is (C=O), $SO_2$ or (CN), provided when $Q_1$ is CN, then X is absent;
wherein $R_4$ is
  (a) H;
  (b) an alkyl of 1 to 6 carbon atoms, inclusive, which may be a straight chain or branched;
wherein $R_5$ is

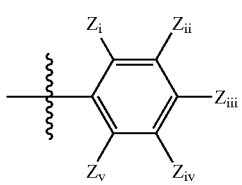

wherein $Z_i$, $Z_{ii}$, $Z_{iii}$, $Z_{iv}$ and $Z_v$, are each independently selected from —$NO_2$, —CN, —C(=O)—$R_T$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
  (a) H;
  (b) an alkyl from 1 to 4 carbon atoms, inclusive, straight chain or branched;
wherein T is O or S; and
pharmaceutically acceptable salts thereof, such that TNFα initiated polymorphoneutrophil (PMN) inflammation is treated in a subject.

2. The method of claim 1, wherein said method is performed in vitro.

3. The method of claim 1, wherein said method is performed in vivo.

4. A method for treating TNFα initiated cytokine inflammation in a subject, comprising
administering to the subject an effective anti-TNFα amount of a lipoxin analog having the formula

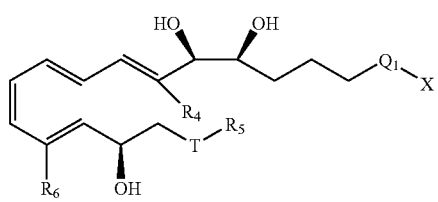

wherein X is $R_1$, $OR_1$, or $SR_1$;
wherein $R_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

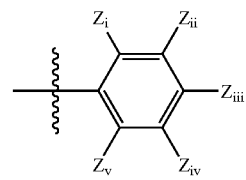

wherein $Z_i$, $Z_{ii}$, $Z_{iii}$, $Z_{iv}$, and $Z_v$, are each independently selected from —$NO_2$, —CN, —C(=O)—$R_T$, —$SO_3H$, a hydrogen atom, halogen, methyl, —$OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;
wherein $R_T$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

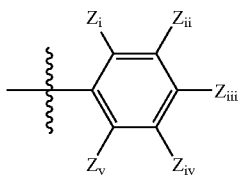

wherein $Z_i$, $Z_{ii}$, $Z_{iii}$, $Z_{iv}$ and $Z_v$, are each independently selected from —$NO_2$, —CN, —$S_3H$, a hydrogen atom, halogen, methyl, —$OR_x$, wherein $R_x$ is 1 to 8 carbon atoms, inclusive, which may be a straight chain or branched, and hydroxyl;

wherein $Q_1$ is (C=O), $SO_2$ or (CN), provided when $Q_1$ is CN, then X is absent;

wherein $R_4$ is
 (a) H;
 (b) an alkyl of 1 to 6 carbon atoms, inclusive, which may be a straight chain or branched;

wherein $R_5$ is

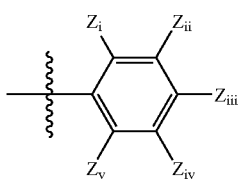

wherein $Z_i$, $Z_{ii}$, $Z_{iii}$, $Z_{iv}$ and $Z_v$, are each independently selected from —$NO_2$, —CN, —C(=O)—$R_T$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
 (a) H;
 (b) an alkyl from 1 to 4 carbon atoms, inclusive, straight chain or branched;

wherein T is O or S; and pharmaceutically acceptable salts thereof, such that TNFα initiated cytokine inflammation is treated in a subject.

5. The method of claim 4, wherein said method is performed in vitro.

6. The method of claim 4, wherein said method is performed in vivo.

7. A method for treating TNFα initiated IL-1β inflammation in a subject, comprising administering to the subject an effective anti-TNFα amount of a lipoxin analog having the formula

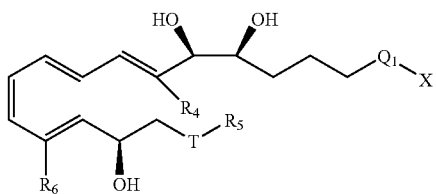

wherein X is $R_1$, $OR_1$ or $SR_1$;
wherein $R_1$ is
 (i) a hydrogen atom;
 (ii) an alkyl of 1 to 8 carbons atoms, inclusive, which may be straight chain or branched;
 (iii) a cycloalkyl of 3 to 10 carbon atoms;
 (iv) an aralkyl of 7 to 12 carbon atoms;
 (v) phenyl;
 (vi) substituted phenyl

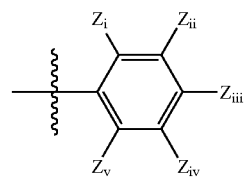

wherein $Z_i$, $Z_{ii}$, $Z_{iii}$, $Z_{iv}$ and $Z_v$, are each independently selected from —$NO_2$, —CN, —C(=O)—$R_T$, —$SO_3H$, a hydrogen atom, halogen, methyl, —$OR_x$, wherein $R_x$ is 1 to 8 carbon atoms, inclusive, which may be a straight chain or branched, and hydroxyl;
 (vii) a detectable label molecule; or
 (viii) a straight or branched chain alkenyl of 2 to 8 carbon atoms, inclusive;
wherein $R_T$ is
 (i) a hydrogen atom;
 (ii) an alkyl of 1 to 8 carbons atoms, inclusive, which may be straight chain or branched;
 (iii) a cycloalkyl of 3 to 10 carbon atoms;
 (iv) an aralkyl of 7 to 12 carbon atoms;
 (v) phenyl;
 (vi) substituted phenyl

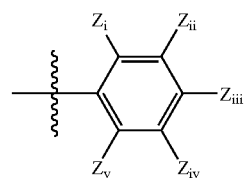

wherein $Z_i$, $Z_{ii}$, $Z_{iii}$, $Z_{iv}$ and $Z_v$, are each independently selected from —$NO_2$, —CN, —$SO_3H$, a hydrogen atom, halogen, methyl, —$OR_x$, wherein $R_x$ is 1 to 8 carbon atoms, inclusive, which may be a straight chain or branched, and hydroxyl;

wherein $Q_1$ is (C=O), $SO_2$ or (CN), provided when $Q_1$ is CN, then X is absent;

wherein $R_4$ is
 (a) H;
 (b) an alkyl of 1 to 6 carbon atoms, inclusive, which may be a straight chain or branched;

wherein $R_5$ is

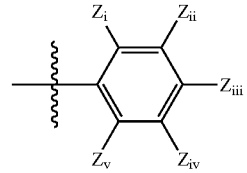

wherein $Z_i$, $Z_{ii}$, $Z_{iii}$, $Z_{iv}$ and $Z_v$, are each independently selected from —$NO_2$, —CN, —C(=O)—$R_T$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;

wherein T is O or S; and pharmaceutically acceptable salts thereof such that TNFα initiated IL-1β inflammation is treated in a subject.

8. The method of claim 7, wherein said method is performed in vitro.

9. The method of claim 7, wherein said method is performed in vivo.

* * * * *